United States Patent [19]
Videen

[11] Patent Number: 6,138,083
[45] Date of Patent: Oct. 24, 2000

[54] SURFACE CONTAMINANT PROBE

[75] Inventor: Gorden Videen, Beltsville, Md.

[73] Assignee: The United States of America as represented by the Secretary of the Army, Washington, D.C.

[21] Appl. No.: 09/134,678

[22] Filed: Aug. 7, 1998

Related U.S. Application Data

[60] Provisional application No. 60/080,854, Apr. 7, 1998.

[51] Int. Cl.[7] .......................... G01B 15/00; G01B 11/08; G01N 15/02
[52] U.S. Cl. ...................... 702/155; 702/157; 702/170; 356/335; 356/336
[58] Field of Search .............................. 702/40, 155, 157, 702/159, 170, 172, 190; 356/335, 336, 364, 367, 368; 382/108; 703/2

[56] References Cited

U.S. PATENT DOCUMENTS

| | | | |
|---|---|---|---|
| 4,306,809 | 12/1981 | Azzam | 356/336 |
| 4,772,126 | 9/1988 | Allemand et al. | 356/368 |

OTHER PUBLICATIONS

Bickel, W. S. et al., "Stokes Vectors, Mueller Matrices, and Polarized Scattered Light", Am. J. Phys., vol. 53, No. 5, pp. 468–478, May 1985.

Iafelice, V. J., et al., "Polarized Light–Scattering Matrix Elements for Select Perfect and Perturbed Optical Surfaces", Applied Optics, vol. 26, No. 12, pp.. 2410–2415, Jun. 15, 1987.

Videen, Gorden, "Light Scattering from a Sphere on or Near a Surface", J. Opt. Soc. Am. A, vol. 8, No. 3, pp. 483–489, Mar. 1991.

Videen, G. et al., "Light Scattering Mueller Matrix for a Surface Contaminated by a Single Particle in the Rayleigh Limit", Optical Engineering, vol. 31, No. 2, pp. 341–349, Feb. 1992.

Videen, Gorden, "Light Scattering from a Particle on or Near a Perfectly Conducting Surface", Optics Communications 115, pp. 1–7, Mar. 1, 1995.

Videen, Gorden et al., "Light Scattering from a Cylinder Near a Plane Interface: Theory and Comparison with Experimental Data", J. Opt. Soc. Am. A, vol. 14, No. 1, pp. 70–78, Jan. 1997.

Videen, Gorden, "Polarized Light Scattering from Surface Contaminants", Optics Communications 143, pp. 173–178, Nov. 15, 1997.

(List continued on next page.)

*Primary Examiner*—Marc S. Hoff
*Assistant Examiner*—Manuel L. Barbee
*Attorney, Agent, or Firm*—Paul S. Clohan, Jr.; Mark D. Kelly

[57] ABSTRACT

A light scattering Mueller matrix for an irregular particle placed on a plane interface is derived using the process of the present invention. The relationships discovered in this derivation are unique because they are independent of the particle shape, and only depend on the substrate refractive index (which is known), the wavelength and angle of incidence of the incident light (also known), and the approximate size of the scatterer (unknown). All that is required to estimate the size of the contaminant is to vary the scatterer size parameter until the model calculations of the light scattering Mueller matrix elements match the experimentally measured light scattering Mueller matrix elements. The probe of the present invention may be used as follows. First, the polarization state of the scattered light can be determined by measuring the Mueller matrix or Jones elements. Next, a "best fit" is made between these elements and the model. This "best fit" may be achieved via a merit function to weight out scattering regions, perhaps near-grazing scattering angles. Particle size is varied in the model until the fit is achieved.

34 Claims, 6 Drawing Sheets

OTHER PUBLICATIONS

Videen, Gorden, "Polarized Light Scattering from Surface Contaminants", Electromagnetic and Light Scattering—Theory and Applications III, Proceedings of the 3rd Workshop on Electromagnetic and Light Scattering—Theory and Applications, Bremen, Germany, pp. 279–286, Mar. 16–17, 1998.

Optics, Eugene Hecht/Alfred Zajac, Fourth printing, Feb. 1979.

Optical Properties of Model Anisotropic Particles on or Near a Perfectly Reflecting Surface, F. Borghese, P. Denti and R. Saija, J. Op Soc Am A/vol. 12, No. 3/Mar. 1995.

Optical Constants, Marvin R. Querry, Ph.D, University of Missouri, Jun. 1985.

Experimental Determinations of Mueller Scattering Matrices for Nonspherical Particles, Roger J. Perry, Arlon J. Hunt and Donald R. Huffman, Applied Optics/vol. 17, No. 17/Sep. 1, 1978.

A New Polarization–Modulated Light Scattering Instrument, Arlon J. Hunt and Donald R. Huffman, vol. 44, No. 12, Dec. 1973.

Scattering by Aggregates with and without an Absorbing Mantle: Microwave Analog Experiments, R.H. Zerull, B.A.S. Gustafson, K. Schulz and E. Thiele–Corbach, Applied Optics, vol. 32 No. 21 Jul. 20, 1993.

Ellipsometry and Polarized Light, R.M.A. Azzam and N.M. Bashara North Holland Personal Library.

SURFACE CONTAMINANT PROBE

CROSS-REFERENCE TO RELATED APPLICATIONS

This application claims priority from Provisional U.S. Patent Application Ser. No. 60/080,854 filed Apr. 7, 1998 and incorporated herein by reference.

STATEMENT OF GOVERNMENT INTEREST

The subject matter of the present application was developed by employees of the U.S. Government, Department of the Army, Army Research Laboratory, in the course of their employment. The U.S. Government has a paid-up license in this invention and the right to require the patent owner to license others on reasonable terms.

FIELD OF THE INVENTION

The present invention relates to the measurement of scattered polarized light for use in a surface contaminant probe for characterizing size and types of surface contaminants or particles.

BACKGROUND OF THE INVENTION

Detecting the presence and types of particle and other types of contaminants or irregularities on surfaces may be useful in many fields. For example, for a space telescope, it may be desirable to be able to detect the presence of dust particles on the surface of a telescope mirror and to be able to distinguish such particles from other imperfections such as micro-meteorite impacts or other defects.

In a more down-to-earth application, in semiconductor manufacturing, it may be useful to be able to detect the presence of contaminant particles on semiconductor wafers and surfaces prior to and during processing. Moreover, it may be useful to be able to distinguish such contaminate particles from surface defects (e.g., pits, crystal defects, and the like) in a semiconductor surface.

Light scattering provides a non-invasive method of analyzing high-quality substrates. Consequently, a great deal of effort has gone into developing theories to predict the scatter from simple contaminants in contact with a substrate. In these theories, an interaction field is generally introduced which is equivalent to the scattered field from the image of the contaminant. The boundary conditions can then be satisfied at the surfaces of the contaminant and the substrate simultaneously. Although in principle the scatter from any contaminant can be solved numerically, it is difficult to characterize contaminants from their resulting scatter.

There have been many experimental and modeling investigations in the prior art to attempt to discover and exploit the behavior of the polarization state of light scattered by particles. The 16-element light-scatter Mueller matrix is a useful tool in polarization analyses because it contains all the scattering information from a scattering system. The polarization elements of this matrix are extremely sensitive to small surface irregularities and can be used to characterize gross properties of a scattering system.

The use of polarized light to investigate particles has been attempted in the art. However, due to the irregular surface structure of particles, effectively modeling scatter response from different particle types and sizes so as to be able to characterize different particle sizes has heretofore been unknown in the art.

SUMMARY OF THE INVENTION

The basic principle of the present invention results from the discovery by the inventor that an irregular particle may have certain polarized light responses similar to that of a Rayleigh dipole located at a corresponding distance from surface. A Rayleigh dipole is a sphere having a diameter much less (e.g., 1/10 or less) than that of the wavelength of incident light. Calculation of the light response of a multi-faceted particle of unknown shape is a nearly impossible task. However, response from a spherical Rayleigh dipole may be more mathematically calculated, due to the regular and symmetrical geometry of a sphere.

Despite the radical differences between the geometries of irregular particles and Rayleigh dipoles, the inventor has discovered that certain scattered light responses for an irregular particle on a surface are similar to that of a Rayleigh dipole located a distance from the surface approximately equal to the mean radius of the particle. The random shape of the particle produces a light scattering effect, such that the polarization state of the scattered light is similar to that of a very small sphere.

From this discovery, the inventor has been able to generate curves modeling the response of a particle of a particular diameter. Series of such curves may be then stored in a computer, and resultant light scatter from a test sample may then be compared with such stored curves to characterize size and type of particle.

The resultant surface contaminant probe may be used to determine the size of irregular contaminants on a high-quality substrate. Such a probe has applications in quality control of computer chip components and in the evaluation of optical components, essentially in any industry in which precision surfaces are fabricated (e.g., using clean room technologies).

The tool in the probe is the light scattering Mueller matrix elements of the scattering system. These elements may be measured in a wide variety of methods. They provide the complete light scattering polarization information of the scattering system, in this case the contaminant on the substrate. One unique aspect is the process by which the scattering information is used to gain information on the particle system.

A light scattering Mueller matrix for an irregular particle placed on a plane interface is derived using the process of the present invention. The relationships discovered in this derivation are unique because they are independent of the particle shape, and only depend on the substrate refractive index (which is known), the wavelength and angle of incidence of the incident light (also known), and the approximate size of the scatterer (unknown). All that is required to estimate the size of the contaminant is to vary the scatterer size parameter until the model calculations of the light scattering Mueller matrix elements match the experimentally measured light scattering Mueller matrix elements. This can be performed, for example, using least-squares fitting, or using a suitable merit function as are known in the art.

Sample calculations are provided below to show that these elements vary sufficiently with contaminant size that they are sensitive. This process may then be used to estimate the size of contaminants on a plane interface using techniques of Iafelice and Bickel, *Appl. Opt.* 26, (1987) 2410, incorporated herein by reference. The model predictions of the particle size were within 5% of the measurements of the particle size given by Iafelice and Bickel.

The probe of the present invention may be used as follows. First, the polarization state of the scattered light can be determined by measuring the Mueller matrix or Jones elements. Next, a "best fit" is made between these elements and the model. This "best fit" may be achieved via a merit function to weight out scattering regions, perhaps near-grazing scattering angles. Particle size is varied in the model until the fit is achieved.

The probe of the present invention uses the polarization state of the scattered light, not the total intensity. Polar nephelometers have been developed to measure the polarization state of the scattered light, but no process has been developed in the prior art to use these measurements to achieve physical information about particles on the substrate. The results achieved by the present invention are independent of the particle shape (only the particle size is important), so long as the particle is sufficiently irregular in shape, as common contaminants (e.g., dust) are.

A model was developed to estimate the polarization state of scattered light from certain surface particulates illuminated at near-grazing incidence. The polarization state of the light scattered by the isolated particle must resemble that of a Rayleigh particle. Although this condition appears constraining, it holds approximately for several particle systems, including Arizona road dust. Arizona road dust is a standardized dust known in the art available to researchers and Engineers for testing purposes.

The model results are independent of the actual shape and refractive index of the contaminant, but are sensitive to the dimensions of the particle and may be used in sizing contaminants on substrates. The sensitivity of the model to contaminant size was examined and compared with experimental results.

DETAILED DESCRIPTION OF THE INVENTION

In the present invention, the Mueller scattering matrix is used as a tool to characterize the scatter from a contaminant on a substrate. A model has been developed which may be used in the inversion process of characterizing contaminants from their resulting scatter. Before developing that model, it is necessary to take a closer look at the contaminants and their scattering properties.

The contaminants considered are irregular particles like dust and soot, which might be modeled as aggregates. Smoke particles, for instance, coagulate into sparse random clusters of Rayleigh-sized spherules. Measurements reveal that the polarization Mueller matrix elements ($S_{12}$, $S_{33}$, and $S_{34}$) for a large aggregate particle consisting of Rayleigh-sized sub-particles resemble those of a Rayleigh particle. Similarly, measurements of the large-amplitude fluctuations characteristic of the polarization matrix elements of a quartz fiber have been observed to evolve into those resembling a Rayleigh particle as the fiber is coated with MgO crystals even though neither the fiber nor the MgO crystals were Rayleigh-sized.

Figure 1:
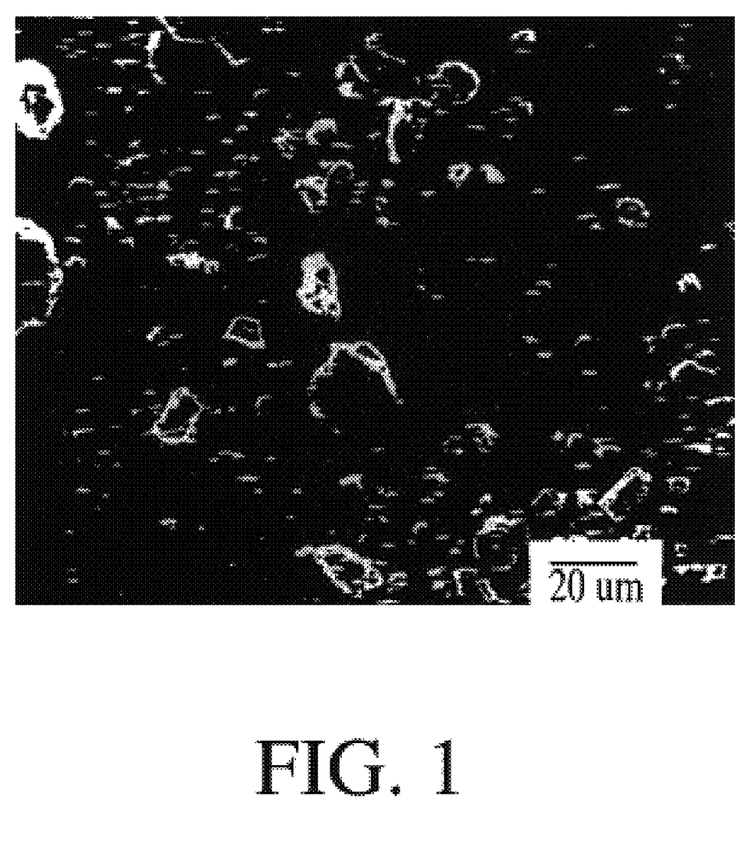
FIG. 1 is a micrograph of standard Arizona Road Dust used as sample particulate in the art.

The similarity between the polarized light scattered by a complex structure and its components holds true for highly irregular particle systems like Arizona road dust, a sample of which is illustrated in FIG. 1. Mueller matrix elements for Arizona road dust have been measured using the polarization modulation techniques developed by A. J. Hunt and D. R. Huffman, *Rev. Sci. Instrum.* 44 (1973) 1753, and R. J. Perry et al. *Appl. Opt.* 17 (1978) 2700, both of which are incorporated herein by reference.

Figure 2A:
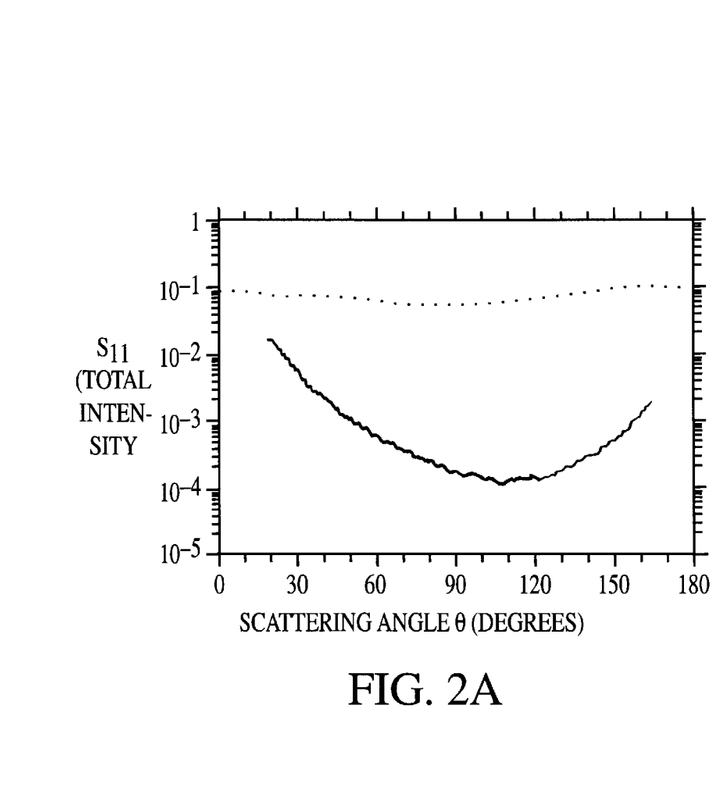
FIG. 2A is a graph illustrating the first (total intensity) of the four non-zero normalized light-scattering Mueller matrix elements for symmetric scatterers shown for Arizona road dust measure at $\lambda=0.4416$ $\mu$m indicated by the solid line as well as the calculated normalized element for a Rayleigh sphere indicated by a dotted line.
Figure 2B:
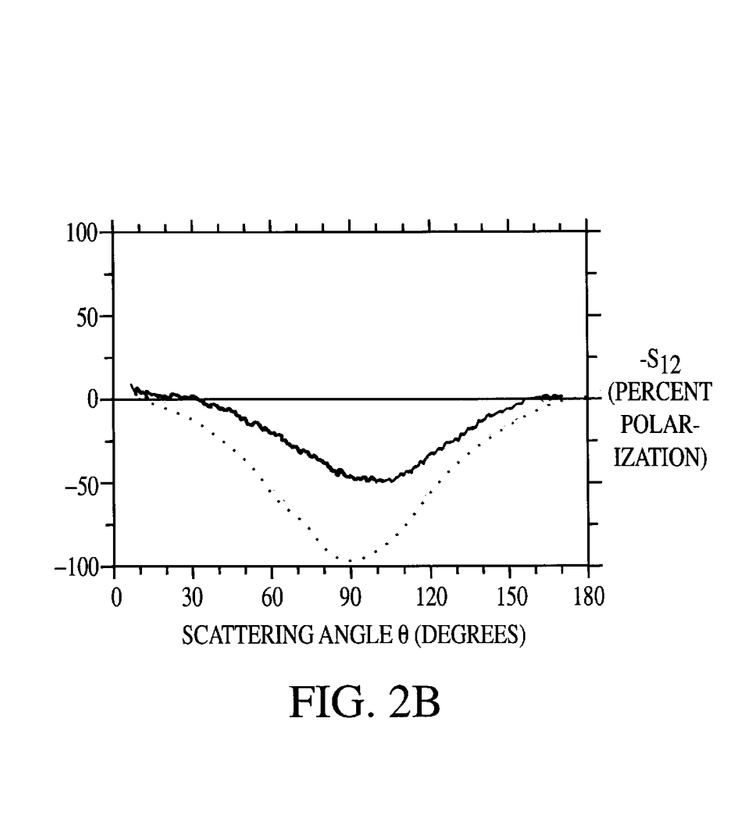
FIG. 2B is a graph illustrating the second ($S_{12}$) of the four non-zero normalized light-scattering Mueller matrix elements for symmetric scatterers shown for Arizona road dust measure at $\lambda=0.4416$ $\mu$m indicated by the solid line as well as the calculated normalized element for a Rayleigh sphere indicated by a dotted line. This element is a measure of the efficiency of the scatterer to scatter vertically or horizontally polarized light in a particular direction.
Figure 2C:
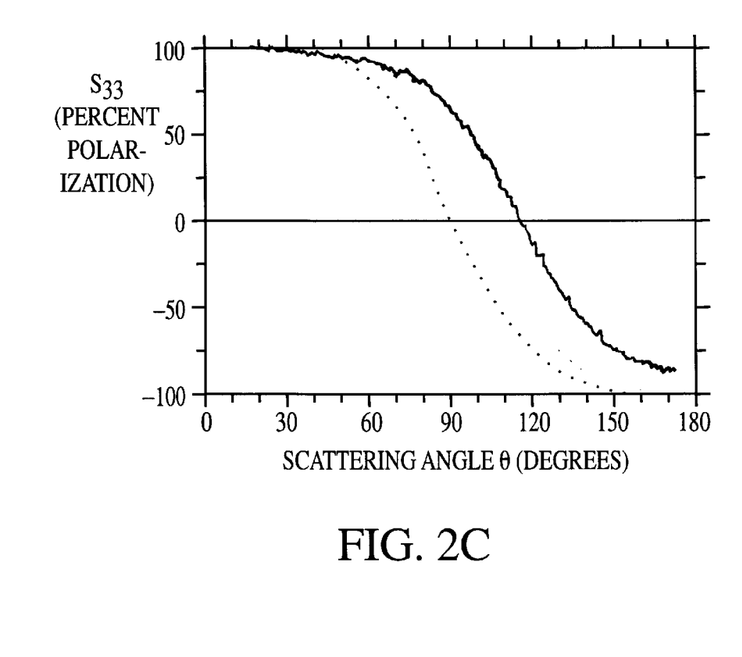
FIG. 2C is a graph illustrating the third ($S_{33}$) of the four non-zero normalized light-scattering Mueller matrix elements for symmetric scatterers shown for Arizona road dust measure at $\lambda=0.4416$ $\mu$m indicated by the solid line as well as the calculated normalized element for a Rayleigh sphere indicated by a dotted line. This element is a measure of the efficiency of the scatterer to keep 45° polarized light in this state in a particular scattering direction.
Figure 2D:
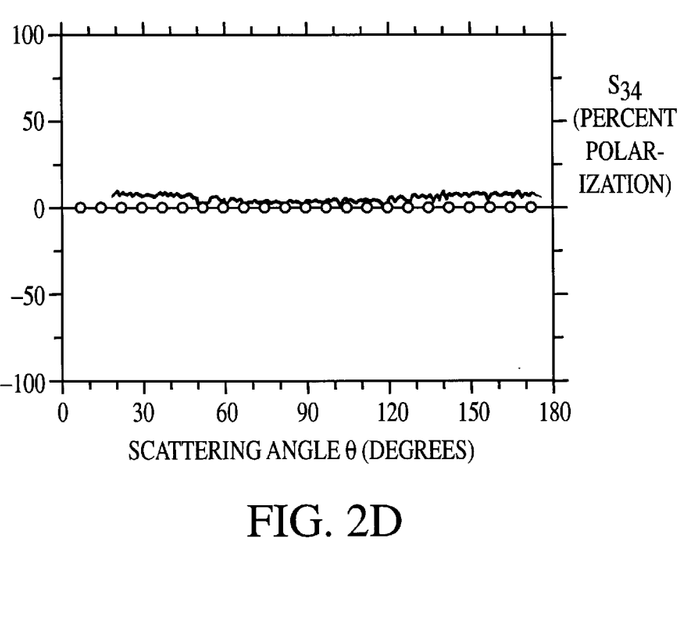
FIG. 2D is a graph illustrating the fourth ($S_{34}$) of the four non-zero normalized light-scattering Mueller matrix elements for symmetric scatterers shown for Arizona road dust measure at $\lambda=0.4416$ $\mu$m indicated by the solid line as well as the calculated normalized element for a Rayleigh sphere indicated by a dotted line. This element is a measure of the efficiency of the scatter to convert circularly polarized light to 45° polarized light in a particular scattering direction.

FIGS. 2A–2D compare Mueller matrix elements for Arizona Road Dust to the elements of a Rayleigh sphere. FIG. 2A illustrates the first Mueller matrix element, $S_{11}$, representing the total intensity of scattered light at different incident angles. FIGS. 2B–2D illustrate the polarization Mueller matrix elements ($S_{12}$, $S_{33}$, and $S_{34}$).

FIG. 2B is a graph illustrating the second ($S_{12}$) of the four non-zero normalized light-scattering Mueller matrix elements for symmetric scatterers shown for Arizona road dust measure at $\lambda=0.4416$ $\mu$m indicated by the solid line as well as the calculated normalized element for a Rayleigh sphere indicated by a dotted line. This element is a measure of the efficiency of the scatterer to scatter vertically or horizontally polarized light in a particular direction.

FIG. 2C is a graph illustrating the third ($S_{33}$) of the four non-zero normalized light-scattering Mueller matrix elements for symmetric scatterers shown for Arizona road dust measure at $\lambda=0.4416$ $\mu$m indicated by the solid line as well as the calculated normalized element for a Rayleigh sphere indicated by a dotted line. This element is a measure of the efficiency of the scatterer to keep 45° polarized light in this state in a particular scattering direction.

FIG. 2D is a graph illustrating the fourth ($S_{34}$) of the four non-zero normalized light-scattering Mueller matrix elements for symmetric scatterers shown for Arizona road dust measure at $\lambda=0.4416$ $\mu$m indicated by the solid line as well as the calculated normalized element for a Rayleigh sphere indicated by a dotted line. This element is a measure of the efficiency of the scatter to convert circularly polarized light to 45° polarized light in a particular scattering direction.

For all four of FIGS. 2A through 2D, the dotted line represents the response of an ideal Rayleigh dipole, whereas the solid line illustrates the response for Arizona road dust.

Even though the dust particles are many times larger than the wavelength, the polarization matrix elements (FIGS. 2B–2D) have characteristics similar to those of the Rayleigh particle; i.e., the characteristic dip in matrix element $S_{12}$, the characteristic S-shape of element $S_{33}$, and element $S_{34}=0$.

The evidence of the particle's size is contained within the total intensity element $S_{11}$ (FIG. 2A). Rather than a symmetric intensity distribution with only a 50% drop-off at $\theta=90°$ as would be expected for a Rayleigh particle, we see a three-order-of-magnitude drop in intensity from the forward scatter followed by an order-of-magnitude rise in intensity in the backscatter. This behavior can be explained by waves emanating from individual scattering sites on the dust particles interfering constructively in the forward-scatter region. The rise in the backward direction can be explained by enhanced backscatter due to rays reflecting off multiple interfaces; i.e., the path difference is the same when the order of the interfaces that the light ray strikes is reversed for backscattered light, and the two (forward and backward traversing) rays interfere constructively, causing the intensity to be increased.

Even though the total scattered intensity (FIG. 2A) does not resemble that of Rayleigh particles, the polarization elements (FIGS. 2B–2D) strongly mimic Rayleigh scattering. This observation is used to model the polarization state of such particles placed on a substrate.

The solution to the scatter from an arbitrarily shaped particle placed in close proximity to a plane interface has recently been formulated by G. Videen, *Opt. Comm.* 115 (1995) 1, and F. Borghese et al. *J. Opt. Soc. Am. A* 12 (1995) 530, both of which are incorporated herein by reference. Although this derivation was derived explicitly for the case of a perfectly conducting substrate, it can easily be modified to accommodate non-perfectly conducting substrates using an approximation described in the prior art. In this approximation, the scattered field emanating from the particle strikes the substrate at normal incidence before again interacting with the particle.

The beauty of this formulation is that the solution to the scatter from the particle on the substrate can be found directly from the T-matrix solution of the same particle when no substrate is present. Because the solution is expressed in terms of spherical harmonic expansions, the scattering and surface interaction may be analyzed as a function of various system parameters.

The interaction field is small compared with the incident field when the refractive index of the substrate is similar to the surrounding medium or when the particle is placed a sufficient distance from the substrate (the intensity of the interaction field decays as the inverse of the square of the particle-substrate separation distance d). Such conditions are desirable in modeling, since the interaction terms cause mode-mixing and the solution for the scattered field can only be achieved through numerically intensive matrix inversions.

If the interaction field is negligible, then the scattered field from a particle on a substrate can be found directly as the superposition of the scattered fields from the particle and the image particle. In the plane defined by the surface normal and the incident wavevector, the scattered field from a particle resting on a surface can be expressed as the superposition of the fields from the particle and image particle, or in terms of the scattering amplitude matrix elements:

$$S_1(\theta-\theta_0)=S_1^0(\theta-\theta_0)+S_1^0(\pi-\theta-\theta_0)R_{TE}(\theta_0)\exp[i\delta(\theta_0,d)]$$
$$+S_1^0(\pi-\theta-\theta_0)R_{TE}(\pi-\theta)\exp[i\delta(\pi-\theta,d)]$$
$$+S_1^0(\theta-\theta_0)R_{TE}(\theta_0)R_{TE}(\pi-\theta)\exp\{i[\delta(\theta_0,d)+\delta(\pi-\theta,d)]\} \quad (1)$$

$$S_2(\theta-\theta_0)=S_2^0(\theta-\theta_0)+S_2^0(\pi-\theta-\theta_0)R_{TM}(\theta_0)\exp[i\delta(\theta_0,d)]$$
$$+S_2^0(\pi-\theta-\theta_0)R_{TM}(\pi-\theta)\exp[i\delta(\pi-\theta,d)]$$
$$+S_2^0(\theta-\theta_0)R_{TM}(\theta_0)R_{TM}(\pi-\theta)\exp\{i[\delta(\theta_0,d)+\delta(\pi-\theta,d)]\} \quad (2)$$

where $\theta$ and $\theta_0$ are the scattering and the incident angles measured from the surface normal, d is the separation distance between the particle and the substrate, $R_{T*}(\theta)$ are the Fresnel reflection coefficients, $$\delta(\theta,d)=-2kd\cos\theta, \quad (3)$$

and $S_1(\theta-\theta_0)$ and $S_2(\theta-\theta_0)$ are the scattering amplitude matrix elements for the isolated particle. Equations 1 and 2 are a direct result of setting the interaction fields equal to zero in the equations describing the scatter from particles on or near substrates.

The ability of a scattering system to polarize light is contained within its light-scattering Mueller matrix elements. The normalized polarization Mueller matrix elements are expressed as:

$$S_{12} = \tfrac{1}{2}(|S_1|^2 - |S_2|^2)/S_{11}, \quad (4)$$

$$S_{33} = Re(S_1 S_2^*)/S_{11}, \quad (5)$$

$$S_{34} = Im(S_2 S_1^*)/S_{11}, \quad (6)$$

where the total intensity matrix element is:

$$S_{11} = \tfrac{1}{2}(|S_1|^2 + |S_2|^2). \quad (7)$$

For highly irregular particles (whose polarization matrix elements resemble those of a Rayleigh particle) resting on a substrate, the condition that the interaction fields are negligible must hold true and Equations 1 and 2 are valid, as there is very little interaction between scattering sites located within the particle itself.

The particle, in effect, acts as a group of individual, non-interacting Rayleigh sub-particles, for which there is interference between the waves emanating from each sub-particle, but very little interaction between the sub-particles. This conclusion is based on the shape of the polarization matrix elements of FIGS. 2B–2D and on the experimental and numerical results of Zerull et al. *Appl. Opt.* 32 (1993) 4088, incorporated herein by reference, in which it was discovered that "gross features of the scattering by aggregates . . . can be interpreted in terms of coherent scattering from the unit [Rayleigh-sized] spheres acting independently of each other."

Essentially, any intra-particle interaction causes the polarization matrix elements to differ from those of a Rayleigh particle. Since there is negligible interaction between sub-particles of the system, it can reasonably be assumed that there would also be negligible interaction between the particle and its image particle when it is placed on a substrate. This conclusion can be reached by one of two ways. First, one can reason that the scattering sites located within the particle are closer to each other than they are to those of the image particle. Since there is negligible intra-particle interaction, inter-particle interaction (interaction between the particle and the image particle) must also be negligible, since the inter-particle distances are greater than the intraparticle distances and the interaction fields decay with the inverse of the square of the separation distances.

Second, one can use the observation that the particle scatter may be modeled as the coherent scattering from individual Rayleigh-sized scatterers. Rayleigh scattering intensities are proportional to $V^2/(\lambda^4 d^2)$, where $V$ is the volume of the particle, $\lambda$ is the incident wavelength and $d$ is the inter-particle distance. Since $\lambda$ is much greater than any intra-particle distance (the Rayleigh criterion) and $d$ must be at least as large as any intra-particle distance, the interaction intensity tends toward zero. The scatter from such systems can therefore be described by Equations 1 and 2.

The scattering amplitude matrix elements for an isolated Rayleigh scattering system are related by:

$$S_2^0(\theta - \theta_0) = \cos(\theta - \theta_0) S_1^0(\theta - \theta_0). \quad (8)$$

Equation 8 is also valid for a conglomeration of non-interacting Rayleigh particles, and is approximately valid for some highly irregular particles (e.g., Arizona road dust). By using the Rayleigh-scattering approximation of Equation 8, $S_2^0(\theta - \theta_0)$ can be expressed in terms of $S_1^0(\theta - \theta_0)$ in Equations 1 and 2.

One final approximation is considered in developing the scattering model. This approximation is that at some particle-coordinate-system location, the scattering amplitude matrix elements for the isolated particle are symmetric; i.e., $$S_1^0(\theta - \theta_0) = S_1^0(\theta_0 - \theta). \quad (9)$$

Such a condition is valid for symmetric particles such as spheres, ellipsoids and dipoles when the coordinate system is at the center of the particle. In addition, the scattering phase function (which is the sum of the magnitudes squared of the scattering amplitude matrix elements) of many particles is also approximately symmetric. The scattering amplitude matrix elements, however, contain phase information of the scattered fields and are dependent on the placement of the particle coordinate system.

For example, if the coordinate system is moved close to one edge of a spherical scatterer, the complex amplitudes of the scattered spherical waves expressed in that coordinate system are no longer symmetric, even though the intensity distribution in the far-field is quite symmetric. For highly irregular systems, Equation 9 may hold some validity at a coordinate system placed at some central location of the particle.

The accuracy of using this approximation is further increased by averaging the scattering amplitudes over some finite area to average out the high-frequency interference structure contained in the scattering amplitude coefficients. This is physically equivalent to having collection optics or a finite-size detector collect the scattered field.

Not all irregular particles are expected to satisfy this condition, however, comparison with experimental results given below shows that this condition is at least partially satisfied for some substrate contaminants.

The polarization state of scattered light for contaminants fulfilling the symmetric-scatterer (equation 9) and the non-interacting Rayleigh scatterer (equation 8) conditions may now be derived. By illuminating the substrate at near-grazing incidence ($\theta_0 \sim \pm 90°$), the scattering amplitudes of the isolated particle [$S_1^0(\theta - \theta_0)$ and $S_2^0(\theta - \theta_0)$] may be factored out of Equations 1 and 2, and completely cancel from the normalized polarization matrix elements (Equations 4–6).

The normalized polarization matrix elements now depend only on the separation distance of the particle from the substrate d, the substrate complex refractive index n, and the incident angle $\theta_0$ (as long as $\theta_0 \sim \pm 90°$). It is important to note that the separation parameter d is the distance from the surface of the substrate to some particle coordinate system location at which the symmetric-scatterer approximation holds. The physical extent of a symmetric scatterer is equal to 2d, since this location must be located at the center of such a particle.

If the particle is not symmetric, it would still be expected to be located near some central location of the particle, so that the particle would have a physical dimension of approximately 2d. With this relation, the model can now be applied to determine the size of contaminants located on substrates by varying the separation distance (particle size) in the model until the polarization state of the scattered light matches the experimentally measured state. A model may now be made of the scattered light of contaminants on a substrate.

Figure 3A:
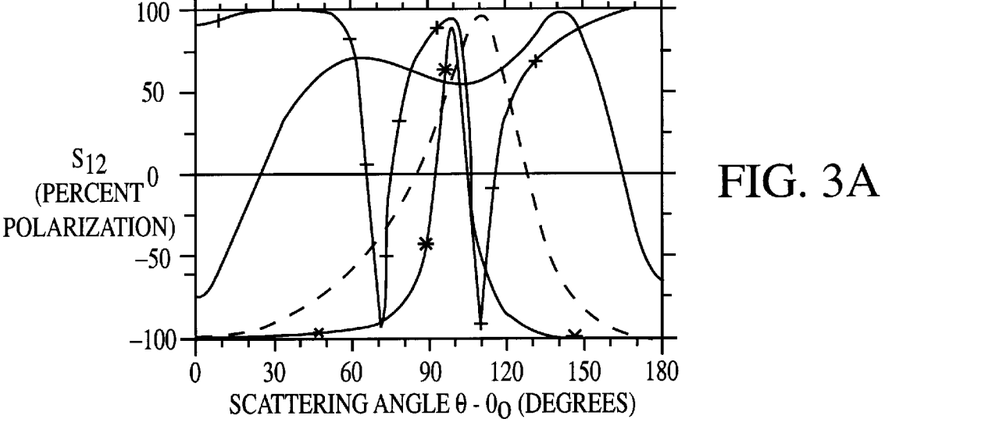
FIG. 3A is a graph illustrating the first ($S_{12}$) (horizontal to vertical polarization) of the three normalized polarization Mueller matrix elements calculated for a symmetric, irregular scatterer placed near an aluminum substrate (n=0.5–5.0i) illuminated at $\theta_0=79°$ by $\lambda=0.4416$ $\mu$m: $d=\lambda/16$, indicated by the * symbols, $d=\lambda/8$, indicated by the dashed line, $d=\lambda/4$, indicated by the solid line, and $d=\lambda/2$, indicated by the + symbols.
Figure 3B:
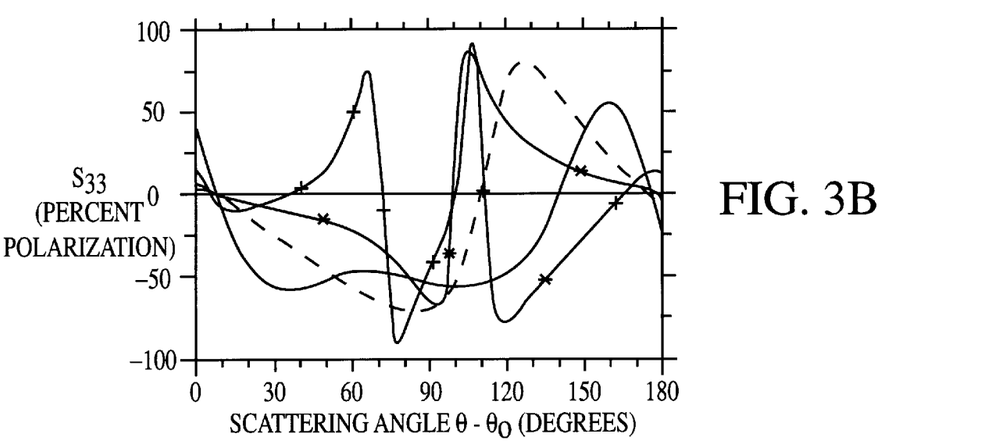
FIG. 3B is a graph illustrating the second ($S_{33}$) of the three normalized polarization Mueller matrix elements calculated for a symmetric, irregular scatterer placed near an aluminum substrate (n=0.5–5.0i) illuminated at $\theta_0=79°$ by $\lambda=0.4416$ $\mu$m: $d=\lambda/16$, indicated by the * symbols, $d=\lambda/8$, indicated by the dashed line, $d=\lambda/4$, indicated by the solid line, and $d=\lambda/2$, indicated by the + symbols.
Figure 3C:
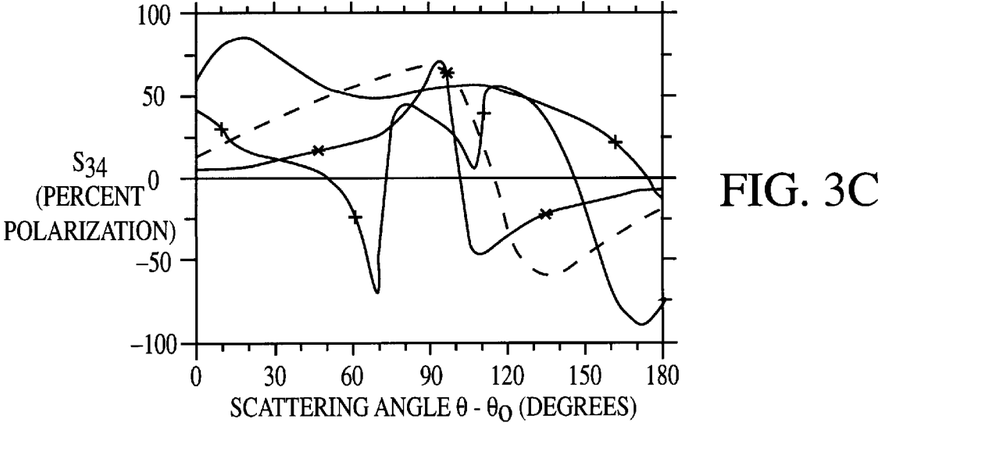
FIG. 3C is a graph illustrating the third ($S_{34}$) of the three normalized polarization Mueller matrix elements calculated for a symmetric, irregular scatterer placed near an aluminum substrate (n=0.5–5.0i) illuminated at $\theta_0=79°$ by $\lambda=0.4416$ $\mu$m: $d=\lambda/16$, indicated by the * symbols, $d=\lambda/8$, indicated by the dashed line, $d=\lambda/4$, indicated by the solid line, and $d=\lambda/2$, indicated by the + symbols.

It is important to know the sensitivity of the polarization state of the scattered light to the system parameters. If the scattered light does not change when the size of the contaminant is varied, then the model is of little use in characterizing contaminants on substrates. The model calculations of the normalized polarization Mueller matrix elements calculated for an irregular, symmetric scatterer placed at four separation distances (corresponding to different-sized contaminants) near an aluminum substrate are shown in FIGS. 3A–C.

It is evident from these Figures that the polarization state of the scattered light is sensitive to the separation distance of the contaminant from the substrate, since all three polarization Mueller matrix elements change significantly at all scattering angles when the separation distance is varied. The model results are now compared with experimentally measured Mueller matrix elements.

Model results were compared with the normalized polarization Mueller matrix elements of select perfect and decayed optical substrates measured by Iafelice and Bickel cited above. These systems are Al-coated sapphire substrates with rms surface roughness $\sigma=1.6\pm0.3$ nm. However, it was noted that surface defects consisting of residual particulates ranging in size from ~0.2 to 1.0 $\mu$m in dimension sparsely littered both substrates. No difference in size distribution was apparent, but the decayed mirror surface had approximately 5 times the number of defects as the perfect mirror surface. The laser light was focused at several different locations on the substrate and sites with large scattering were avoided in making measurements; so it is likely that only one of the smaller scatterers was illuminated when measurements were taken.

Figure 4A:
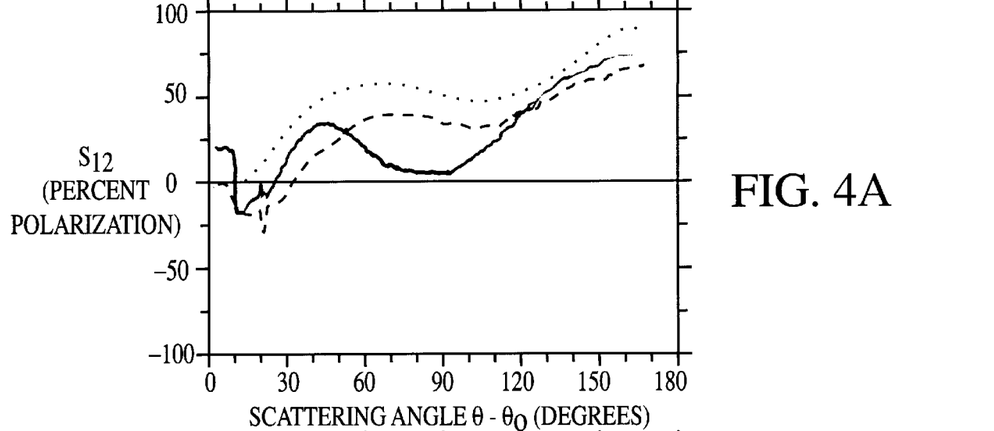
FIG. 4A is a graph illustrating the first ($S_{12}$) of the three normalized polarization Mueller matrix elements calculated for asymmetric, irregular scatterer a distance $d=\lambda/4.7$ from a substrate (n=0.5–3.5i) illuminated at $\theta_0=79°$, indicated by dotted line, and superimposed with the experimental matrix elements of a perfect mirror surface, indicated by the solid line, and decayed mirror surface, indicated by the dashed line, for $\lambda=0.4416$ $\mu$m.
Figure 4B:
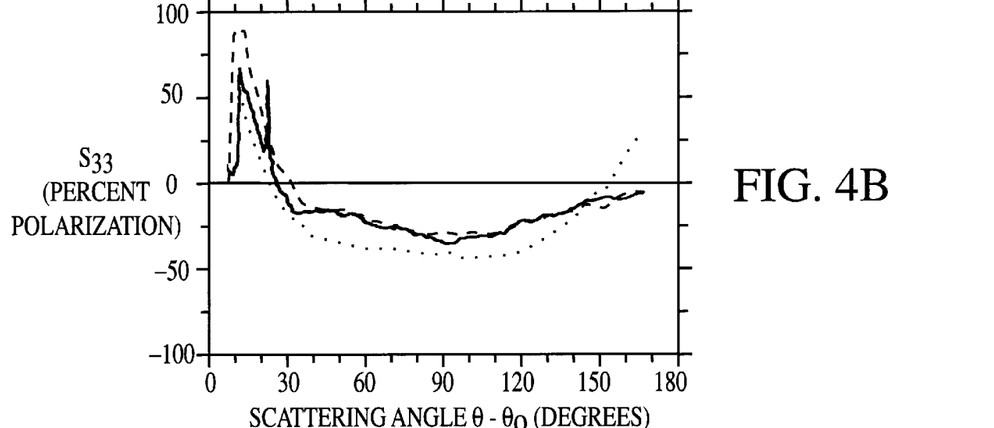
FIG. 4B is a graph illustrating the second ($S_{33}$) of the three normalized polarization Mueller matrix elements calculated for a symmetric, irregular scatterer a distance $d=\lambda/4.7$ from a substrate (n=0.5–3.5i) illuminated at $\theta_0=79°$, indicated by dotted line, and superimposed with the experimental matrix elements of a perfect mirror surface, indicated by the solid line, and decayed mirror surface, indicated by the dashed line, for $\lambda=0.4416$ $\mu$m.
Figure 4C:
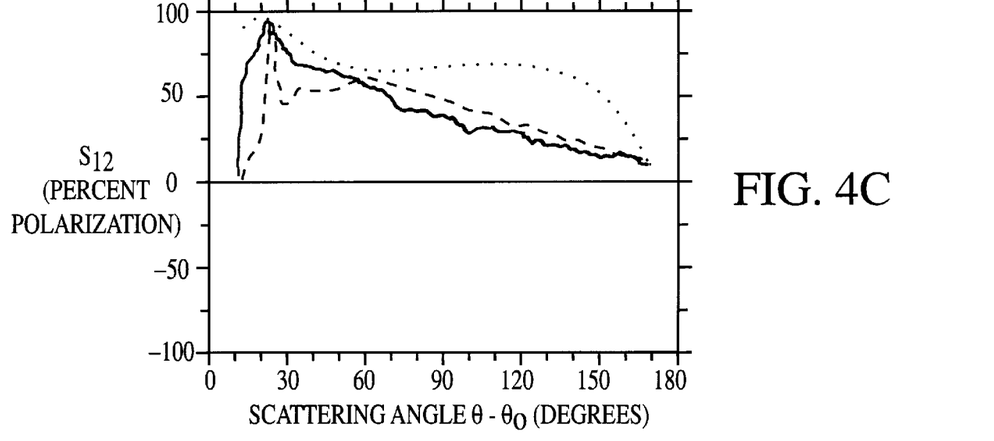
FIG. 4C is a graph illustrating the third ($S_{34}$) of the three normalized polarization Mueller matrix elements calculated for a symmetric, irregular scatterer a distance $d=\lambda/4.7$ from a substrate (n=0.5–3.5i) illuminated at $\theta_0=79°$, indicated by dotted line, and superimposed with the experimental matrix elements of a perfect mirror surface, indicated by the solid line, and decayed mirror surface, indicated by the dashed line, for $\lambda=0.4416$ $\mu$m.

The polarized Mueller matrix elements measured at near-grazing incidence ($\theta_0=79°$) with $\lambda=0.4416$ $\mu$m are illustrated in FIGS. 4A–C, indicated by dotted line, and superimposed with the experimental matrix elements of a perfect mirror surface, indicated by the solid line, and decayed mirror surface, indicated by the dashed line. Also shown are the polarization matrix elements for a symmetric scatterer at a separation distance $d=\lambda/4.7$ from the (n=0.5–3.5i) substrate.

Note that the substrate refractive index is highly dependent on the thickness of the aluminum oxide layer which forms on the surface and acts as an anti-reflection coating and this value is reasonable: values for pure Al are on the order of n=0.5–5.0i; yet Querry in *Optical Constants,* CRDC-CR-85034 (1985), incorporated herein by reference, measured n=0.5–4.5i for Al with a thin layer of aluminum oxide.

Videen and Ngo *J. Opt. Sci. Am. A* 14 (1997) 70, incorporated herein by reference, compared theoretical and experimental Mueller matrix elements of a cylinder resting on a substrate prepared using the same method as Iafelice and Bickel and found best fits for n=0.5–3.8i.

The separation distance ($d=\lambda/4.7$) corresponds to particles having dimension of ~0.2 $\mu$m which is at the lower end of the estimated size range. Overall, the fit of the model results to measurement is good. Model calculations of matrix element $S_{12}$ bear a striking resemblance with those of the decayed mirror surface (increasing the separation distance slightly also produces the hump at $\theta-\theta_0\sim85°$ for the perfect mirror surface). The general shapes of measurement and model results for matrix elements $S_{33}$ and $S_{34}$ are also in good agreement.

From FIGS. 4A–C, it may be seen that the experimental data (indicated by the dashed line) behaves somewhat similarly to that model data (dotted line) and yet is distinguishable from experimental data from a perfect mirror surface (solid line). Thus, an apparatus may be readily constructed to detect the size, presence, and type of particle present on a substrate, and moreover distinguish such particles from other light-scattering phenomena (e.g., defects in the substrate or the like).

Figure 5:
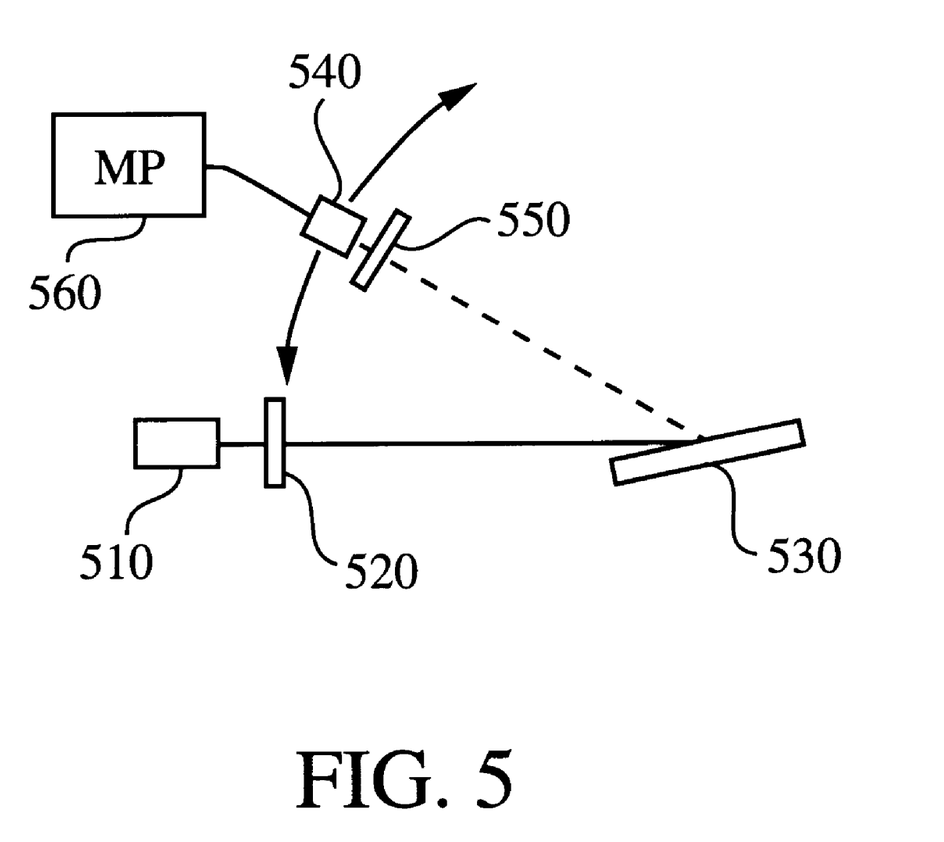
FIG. 5 is a block diagram illustrating the major components of a particle detecting probe.

FIG. 5 is a block diagram illustrating the major components of such a particle detecting probe. Laser 510 directs a beam of light polarized by polarizer 520 towards target 530. Scattered light from target 530 is received by sensor 540 which may comprise a photodiode array or similar sensor provided with polarizing filter 550. Sensor 540 may be selectively located at an angle from 0° to 180° from target 530, or scanned through a range of scattering angles.

Data from sensor 540 may be fed to computer 560 via suitable instrumentation (A/D converter and the like) which may compare data responses from one or more polarized Mueller matrix elements with stored curves such as those illustrated in FIGS. 3A–C. Using curve-fitting techniques known in the art, computer 560 may make a best fit determination between received data and stored model curves. Based upon this determination, computer 560 may determine the size and possibly the type of particle present (if any) on the substrate of sample target 530.

Such a probe may be used to automatically inspect, for example, semiconductor substrates, telescope mirrors, and the like, for presence of particles or defects. If particles are present, it may be possible to remove such particles through cleaning. However, if defects are present, it may be necessary to replace the substrate or telescope mirror.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

For example, as noted in the Background of the Invention, there are a total of sixteen Mueller matrix elements, of which four ($S_{11}$, $S_{12}$, $S_{33}$, and $S_{34}$) are discussed above, with the latter three being of interest. However not all the other elements are of no interest. Mueller matrix element $S_{43}$, for example equals $S_{34}$. Thus, one could measure Mueller matrix $S_{43}$ to determine particle size using the same or similar techniques as described above.

There are other Mueller matrix elements which may also be used as alternatives to the examples discussed above. For example, $S_{12}$ is equal to $S_{21}$, $S_{44}$ is equal to $S_{33}$, and $S_{43}$ is equal to $S_{34}$. Matrix element $S_{21}$ is a measure of the tendency of a scatterer to convert unpolarized light to vertically polarized light and is equivalent to Mueller matrix element $S_{12}$ in the present invention. Matrix element $S_{44}$ is a measure of efficiency of a scatterer to keep circularly polarized light in this state and is equivalent to Mueller matrix element $S_{33}$ in the present invention. Matrix element $S_{43}$ is a measure of the efficiency of a scatterer to convert circularly polarized light to 45° polarized light and is equivalent to Mueller matrix element $S_{34}$ in the present invention. Other Mueller matrix elements with similar responses to those outlined above may also be adapted to the present invention.

It should also be noted that the there are many experimental techniques for measuring Mueller matrices. The apparatus outlined in FIG. 5 is provided for illustrative purposes. Other techniques may also be applied without departing from the spirit and scope of the present invention.

For example, an optical modulator may be used to adjust the polarization state rather than physically rotating the polarizer. Alternately, light may be passed through a beam splitter and different polarization states may be simultaneously measured.

What is claimed is:

1. A method for determining size of irregular particles on a surface, comprising the steps of:

creating and storing a mathematical model of scattered light behavior for irregular particles by calculating polarization states of scattered light from a Rayleigh dipole located at a series of discrete locations from a surface using Mueller matrix or Jones matrix elements to produce a series of curves;

directing a polarized light beam on a surface having irregular particles thereon;

measuring scattered light from the surface and the irregular particles;

determining the polarization state of the scattered light by measuring Mueller matrix or Jones matrix elements;

making a best fit between the Mueller matrix or Jones matrix elements and the curves of the mathematical model; and determining particle size based upon the distance of the Rayleigh dipole from the surface for the curve of the mathematical model having the best fit.

2. The method of claim 1, wherein said step of making a best fit comprises the step of making a best fit between the Mueller matrix or Jones matrix elements and curves of the mathematical model using a merit function to weight out scattering regions.

3. The method of claim 2, wherein the surface is illuminated at near-grazing incidence.

4. The method of claim 1, wherein said step of making a best fit comprises the step of making a best fit between the Mueller matrix or Jones matrix elements and curves of the mathematical model using a simple least-squares technique to weight out scattering regions.

5. The method of claim 4, wherein the surface is illuminated at near-grazing incidence.

6. The method of claim 1, wherein said step of making a best fit comprises the step of making a best fit between the Mueller matrix or Jones matrix elements and curves of the mathematical model using each entire curve of each mathematical model to weight out scattering regions.

7. The method of claim 6, wherein the surface is illuminated at near-grazing incidence.

8. The method of claim 1, wherein said curves of the mathematical model comprise a series of polarization Mueller matrix curves for a Rayleigh dipole located at a corresponding series of discrete distances from the surface.

9. The method of claim 8, wherein said polarization Mueller matrix curves comprise at least a first curve representing the efficiency of the scatterer to scatter vertically or horizontally polarized light in a particular direction.

10. The method of claim 9, wherein said polarization Mueller matrix curves comprise Mueller matrix element $S_{12}$.

11. The method of claim 9, wherein said polarization Mueller matrix curves comprise Mueller matrix element $S_{21}$.

12. The method of claim 8, wherein said polarized Mueller matrix curves comprise at least a first curve representing the efficiency of the scatterer to keep 45° polarized light in this state in a particular scattering direction.

13. The method of claim 12, wherein said polarization Mueller matrix curves comprise Mueller matrix element $S_{33}$.

14. The method of claim 12, wherein said polarization Mueller matrix curves comprise Mueller matrix element $S_{44}$.

15. The method of claim 8, wherein said polarized Mueller matrix curves comprise at least a first curve representing the efficiency of the scatterer to convert circularly polarized light to 45° polarized light in a particular scattering direction.

16. The method of claim 15, wherein said polarization Mueller matrix curves comprise Mueller matrix element $S_{34}$.

17. The method of claim 15, wherein said polarization Mueller matrix curves comprise Mueller matrix element $S_{43}$.

18. An apparatus for determining size of irregular particles on a surface, comprising:

means for creating and storing a mathematical model of scattered light behavior for irregular particles by calculating polarization states of scattered light from a Rayleigh dipole located at a series of discrete locations from a surface using Mueller matrix or Jones matrix elements to produce a series of curves;

means for directing a polarized light beam on a surface having irregular particles thereon;

means for measuring scattered light from the surface and the irregular particles;

means for determining the polarization state of the scattered light by measuring Mueller matrix or Jones matrix elements;

means for making a best fit between the Mueller matrix or Jones matrix elements and the curves of the mathematical model; and means for determining particle size based upon the distance of the Rayleigh dipole from the surface for the curve of the mathematical model having the best fit.

19. The apparatus of claim 18, wherein said means for making a best fit comprises means for making a best fit between the Mueller matrix or Jones matrix elements and curves of the mathematical model using a merit function to weight out scattering regions.

20. The apparatus of claim 19, wherein the surface is illuminated at near-grazing incidence.

21. The apparatus of claim 18, wherein said means for making a best fit comprises means for making a best fit between the Mueller matrix or Jones matrix elements and curves of the mathematical model using a simple least-squares technique to weight out scattering regions.

22. The apparatus of claim 21, wherein the surface is illuminated at near-grazing incidence.

23. The apparatus of claim 18, wherein said means for making a best fit comprises means for making a best fit between the Mueller matrix or Jones matrix elements and curves of the mathematical model using each entire curve of each mathematical model to weight out scattering regions.

24. The apparatus of claim 23, wherein the surface is illuminated at near-grazing incidence.

25. The apparatus of claim 18, wherein said curves of the mathematical model comprise a series of polarization Mueller matrix curves for a Rayleigh dipole located at a corresponding series of discrete distances from the surface.

26. The apparatus of claim 25, wherein said polarization Mueller matrix curves comprise at least a first curve representing the efficiency of the scatterer to scatter vertically or horizontally polarized light in a particular direction.

27. The apparatus of claim 26, wherein said polarization Mueller matrix curves comprise Mueller matrix element $S_{12}$.

28. The apparatus of claim 26, wherein said polarization Mueller matrix curves comprise Mueller matrix element $S_{21}$.

29. The apparatus of claim 25, wherein said polarized Mueller matrix curves comprise at least a first curve representing the efficiency of the scatterer to keep 45° polarized light in this state in a particular scattering direction.

30. The apparatus of claim 29, wherein said polarization Mueller matrix curves comprise Mueller matrix element $S_{33}$.

31. The apparatus of claim 29, wherein said polarization Mueller matrix curves comprise Mueller matrix element $S_{44}$.

32. The apparatus of claim 25, wherein said polarized Mueller matrix curves comprise at least a first curve representing the efficiency of the scatterer to convert circularly polarized light to 45° polarized light in a particular scattering direction.

33. The apparatus of claim 32, wherein said polarization Mueller matrix curves comprise Mueller matrix element $S_{34}$.

34. The apparatus of claim 32, wherein said polarization Mueller matrix curves comprise Mueller matrix element $S_{43}$.

* * * * *